(12) United States Patent
Zaltsberg et al.

(10) Patent No.: US 9,060,863 B2
(45) Date of Patent: Jun. 23, 2015

(54) THREE DIMENSIONAL STRUCTURAL SUPPORT FOR FEMALE PELVIC ORGANS IN THONG UNDERWEAR

(71) Applicant: LevElena Enterprises, Inc., Richardson, TX (US)

(72) Inventors: Lev Zaltsberg, Dallas, TX (US); Elena Zaltsberg, Dallas, TX (US)

(*) Notice: Subject to any disclaimer, the term of this patent is extended or adjusted under 35 U.S.C. 154(b) by 5 days.

(21) Appl. No.: 14/056,833

(22) Filed: Oct. 17, 2013

(65) Prior Publication Data

US 2014/0230826 A1 Aug. 21, 2014

Related U.S. Application Data

(63) Continuation of application No. 13/771,923, filed on Feb. 20, 2013, now abandoned.

(51) Int. Cl.
*A61F 2/24* (2006.01)
*A61F 5/28* (2006.01)
(Continued)

(52) U.S. Cl.
CPC .............. *A61F 5/30* (2013.01); *A61F 5/0093* (2013.01); *A61F 13/15* (2013.01); *A61F 13/472* (2013.01); *A61F 13/66* (2013.01); *A61F 13/476* (2013.01); *A61F 13/04* (2013.01); *A61F 13/496* (2013.01); *A61F 13/49017* (2013.01); *A61F 13/64* (2013.01); *A61F 13/551* (2013.01); *A61F 13/475* (2013.01); *A61F 13/474* (2013.01); *A61F 13/36* (2013.01); *A41B 9/04* (2013.01); *A61F 13/622* (2013.01); *A61F 13/47* (2013.01);
(Continued)

(58) Field of Classification Search
CPC ......... A41B 9/04; A61F 5/0093; A61F 13/04;
A61F 13/15; A61F 13/36; A61F 13/47;
A61F 13/64; A61F 13/66; A61F 13/472;
A61F 13/474; A61F 13/475; A61F 13/476;
A61F 13/495; A61F 13/496; A61F 13/551;
A61F 13/5622; A61F 13/49017; A61F 13/49413
USPC ......... 128/98.1, 99.1, 106.1, 112.1, 846, 888, 128/891; 604/385.01, 385.22, 385.24, 604/385.26, 396, 400, 402
See application file for complete search history.

(56) References Cited

U.S. PATENT DOCUMENTS 5,415,650 A * 5/1995 Sigl ............................... 604/387
5,683,373 A * 11/1997 Darby ....................... 604/385.01
(Continued)

OTHER PUBLICATIONS

PCT International Search Report and Written Opinion in Application No. PCT/US2014/013507 dated Jun. 13, 2014.

*Primary Examiner* — Victoria J Hicks
*Assistant Examiner* — Brandon L Jackson

(57) ABSTRACT

A thin disposable insert for adherence onto the crotch portion of a female undergarment for reducing pressure otherwise transferred from the undergarment to the external genital organs of the female is referred to as a panty guard. An anatomically correctly shaped pelvic organ support included within or adhered to the panty guard provides three dimensional support to the pelvic floor of a female. The pelvic organ support and the thin disposable insert provide a barrier between the female pelvic organs and abrasive fabrics of the undergarment. The pelvic organ support provides a porous space between tight-fitting non-breathable undergarments and the genitalia of the wearer, allowing air to flow across the wearer's skin. The panty guard with a pelvic organ support to prevent infection, lacerations, pelvic floor prolapse, and incontinence.

18 Claims, 3 Drawing Sheets

(51) Int. Cl.
| | |
|---|---|
| *A61F 5/30* | (2006.01) |
| *A61F 5/37* | (2006.01) |
| *A61F 13/00* | (2006.01) |
| *A61F 13/15* | (2006.01) |
| *A61F 13/472* | (2006.01) |
| *A61F 13/66* | (2006.01) |
| *A61F 13/476* | (2006.01) |
| *A61F 13/04* | (2006.01) |
| *A61F 13/496* | (2006.01) |
| *A61F 13/49* | (2006.01) |
| *A61F 13/64* | (2006.01) |
| *A61F 13/551* | (2006.01) |
| *A61F 13/475* | (2006.01) |
| *A61F 13/474* | (2006.01) |
| *A61F 13/36* | (2006.01) |
| *A61F 13/62* | (2006.01) |
| *A61F 13/47* | (2006.01) |
| *A61F 13/494* | (2006.01) |
| *A61F 5/00* | (2006.01) |
| *A41B 9/04* | (2006.01) |
| *A61F 5/455* | (2006.01) |

(52) U.S. Cl.
 CPC ........... *A61F 13/49413* (2013.01); *A61F 5/455* (2013.01)

(56) References Cited

U.S. PATENT DOCUMENTS

| | | | |
|---|---|---|---|
| 5,729,835 A * | 3/1998 | Williams | 2/406 |
| 6,448,465 B1 | 9/2002 | Gustafsson | |
| 6,572,597 B1 * | 6/2003 | Nash | 604/385.05 |
| 6,632,210 B1 * | 10/2003 | Glasgow et al. | 604/385.17 |
| 7,166,307 B1 * | 1/2007 | Ahn et al. | 424/725 |
| 7,927,322 B2 * | 4/2011 | Cohen et al. | 604/385.03 |
| 8,292,862 B2 * | 10/2012 | Dennis et al. | 604/385.03 |
| 8,445,570 B2 * | 5/2013 | Sakata et al. | 524/195 |
| 2001/0025140 A1 * | 9/2001 | Torok et al. | 600/367 |
| 2001/0025163 A1 * | 9/2001 | Brown et al. | 604/385.17 |
| 2002/0193758 A1 | 12/2002 | Sandberg | |
| 2003/0004484 A1 * | 1/2003 | Hammons et al. | 604/385.04 |
| 2003/0097109 A1 * | 5/2003 | Bruce et al. | 604/385.01 |
| 2005/0090795 A1 * | 4/2005 | Coleman | 604/387 |
| 2006/0264884 A1 * | 11/2006 | Carstens | 604/396 |
| 2007/0142816 A1 * | 6/2007 | Carstens | 604/396 |
| 2008/0119815 A1 * | 5/2008 | Carstens | 604/385.24 |
| 2010/0324522 A1 * | 12/2010 | Carstens | 604/385.24 |
| 2010/0324525 A1 * | 12/2010 | Carstens | 604/396 |
| 2010/0324526 A1 * | 12/2010 | Carstens | 604/396 |
| 2011/0092945 A1 * | 4/2011 | Carstens | 604/387 |

\* cited by examiner

THREE DIMENSIONAL STRUCTURAL SUPPORT FOR FEMALE PELVIC ORGANS IN THONG UNDERWEAR

CROSS-REFERENCE TO RELATED APPLICATION(S) AND CLAIM OF PRIORITY

The present application is an continuation of U.S. patent application Ser. No. 13,771,923, filed Feb. 20, 2013, entitled "THREE DIMENSIONAL STRUCTURAL SUPPORT FOR FEMALE PELVIC ORGANS IN THONG UNDERWEAR". This application hereby claims the benefit and/or priority of said application Ser. No. 13/771,926, and hereby incorporates them by reference as if fully set forth herein.

TECHNICAL FIELD

The present application relates generally to supporting the pelvic floor of female anatomy, and more specifically, to a system and method for supporting the pelvic floor of female anatomy within thong underwear.

BACKGROUND

Female underwear is generally intended to provide coverage for the female external genital organs. Female external genital organs include the prepuce of clitoris, clitoris, frenulum, vestibule, Urethra, hymen, fossa navicularis, fourchette, para-urethral duct, labia minora, and labia major. Certain female underwear is also intended to cover the buttocks.

A top view of the female pelvis shows a wider diameter and a more circular shape than that of the male. The wideness facilitates parturition, yet also predisposes women to post-birth pelvic floor weakness. The minor pelvis is the narrower continuation of the major pelvis inferiorly. The inferior pelvic outlet is closed by the pelvic floor. The levator ani and coccygeus muscles that are attached to the inner surface of the minor pelvis form the muscular floor of the pelvis. The pelvic floor (also referred to as pelvic diaphragm) also comprises the connective tissue associated with the levator ani and coccygeus muscles that span the area under the pelvis. The female pelvic organs, within the pelvis, are not upwardly supported by any bones disposed inferiorly (lowerly). The female pelvic organs supported by the muscular pelvic floor include the female genitalia, bladder, and rectum.

Undergarments for females include a variety of shapes and fits. Generally female underwear includes a waistband, a front portion, a crotch portion, and a rear portion. Certain styles of undergarments tend to show lines through tight, close-fitting clothing, such as Spandex®. For example, briefs, bikinis, and boyshorts style underwear reveal a pantyline at the edge and/or edge seam of the underwear. Thong-style underwear (including a g-string, v-string, c-string, tanga, or T-back) (together, hereinafter "thong") do not include a front portion and do not cover the buttocks. In thong underwear, when worn properly by a wearer, the waistband encircles the waist of the wearer; the crotch portion extends downward from the front of the waistband and positions over the crotch of the wearer. The rear portion extends from the rear of the waistband to the posterior end of the crotch portion, where the crotch and rear portions attach. The rear portion of a thong includes a string, thin band or a thin strip of fabric that fits between the buttocks of the wearer. Also, thongs have an abbreviated crotch portion, which have a substantially narrower posterior end compared to the anterior end. Thereby, thongs reduce the appearance of pantylines.

SUMMARY OF THE INVENTION

A system and apparatus capable of providing structural support to thong underwear and pelvic floor support to female pelvic anatomy is provided. In a first embodiment, an apparatus includes a frame configured to maintain a shape of the pelvic organ support apparatus. The shape includes at least one front vertex, and at least two rear vertices. The shape of the apparatus is contoured to the shape of external female genital organs. The apparatus includes a moldable filling material surrounded by the frame. The top of the apparatus is configured to be placed in physical contact with external female genital organs. The frame and filling are configured to support the pelvic floor of a female.

In another embodiment, an apparatus for maintaining the structural integrity of a thong undergarment is provided. The apparatus includes a pad configured to be adhered to the body-contacting side of the crotch portion of thong underwear. The apparatus includes an adhesive strip disposed on a bottom of the pad. The pad is composed of a material that provides a stiffening of the crotch portion of the thong underwear. The shape of the pad includes at least one rear vertex wide enough to prevent unintentional detachment of the at least one rear vertex from the thong undergarment.

A system for supporting the pelvic floor and protecting pelvic organs is provided. The system includes one of a panty liner or a panty guard for maintaining the structural integrity of a thong undergarment. The panty guard includes a pad configured to be adhered to the body-contacting side of the crotch portion of thong underwear. The panty guard includes an adhesive strip disposed on a bottom of the pad. The pad of the panty guard is composed of a material that provides a stiffening of the crotch portion of the thong underwear. The shape of the panty guard includes at least one rear vertex wide enough to prevent unintentional detachment of the at least one rear vertex from the thong undergarment, once adhered. The pantyliner or the panty guard includes a top layer and a lower layer. The system includes a pelvic organ support disposed between the top layer and the lower layer of the pantyliner or the panty guard. The pelvic organ support includes a frame configured to maintain a shape of the pelvic organ support. The frame includes the top layer of the pantyliner or the panty guard. The shape of the pelvic organ support includes at least one front vertex, and at least two rear vertices. The shape of the pelvic organ support is contoured to the shape of external female genital organs. The pelvic organ support includes a moldable filling material. The top of the pelvic organ support is substantially covered by the top layer of the pantyliner or the panty guard. The top surface of the system is configured to be placed in physical contact with external female genital organs. The bottom of the pelvic organ support is substantially covered by the lower layer of the pantyliner or the panty guard. The frame and filling of the pelvic organ support are co figured to support the pelvic floor of a female.

Before undertaking the DETAILED DESCRIPTION OF THE INVENTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term. "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. The phrase "at least one of," when used with a list of items, means that different combinations of one or more of the listed items may be used, and only one item in the list may be needed. For example, "at least one of: A, B, and C" includes any of the following combinations: A; B; C; A and B; A and C; B and C; and A and B and C. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made in which like reference numbers represent like parts.

DETAILED DESCRIPTION

Figure 1:
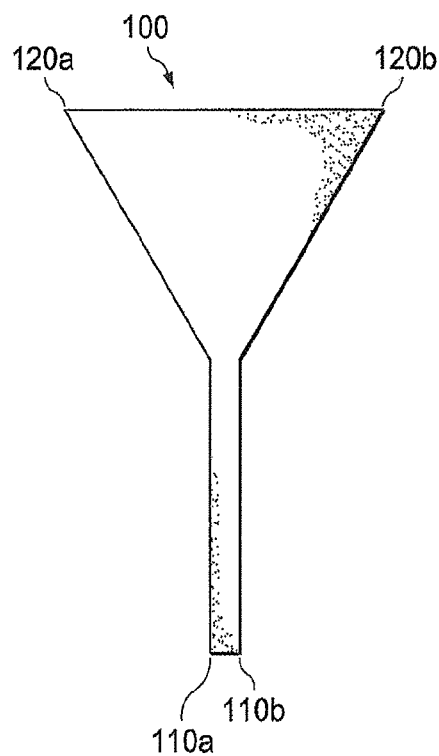
FIGS. 1 and 2 illustrate various designs of a pantyliner.

FIGS. 1 through 7, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged system.

Certain thong-style underwear (hereinafter "thong") are manufactured from materials that comprise chemical fibers and synthetic fibers of low air permeability. Some people who wear thongs experience an allergic reaction to these chemical or synthetic fibers and develop hemorrhoids (also known as skin piles) or vaginitis.

Thongs often include a seam where the rear portion of the underwear attaches to the crotch portion. When the thong is worn by a wearer, the seam of the rear and crotch portions is generally placed on or near the wearer's perineum. As a result of bodily movement, the thin string of the rear portion and the seam binding the rear and crotch portions rub, and thereby damage the skin of the wearer's perineum and nearby external genitalia. Thong wearers experience skin inflammation from the rubbing.

In some thongs, the rear portion of the underwear includes a thin string that pulls tautly during wear and applies pressure to the wearer's perineum. The thin string rear portion fits closely against the wearer's skin between the buttocks. The thin string absorbs fecal bacteria from the anal area, and channels the bacteria to the vagina and urethra. That is, fluid travels between the anal area and the vaginal area via the tightly-fitted rear portion of the thong. The bacteria channeling effect of the rear portion of the thong produces conditions for urinary tract infection and vaginal infection. The loose fit of the rear portion of briefs and bikini style underwear reduces the channeling affect.

The tight fit of the thong limits air flow to the covered body parts. As a result of bodily movement, the crotch portion rubs against the urethra and other female external genital organs. The rubbing and pressure of the rear and crotch portions of the thong cause skin inflammation (including swelling) and small lacerations, which lead to infection. When a wearer exercises, the combination of sweat and limited air flow creates an environment for vaginal yeast infection. A thong manufactured from non-breathable material, as opposed to cotton, further ripens the conditions for vaginal yeast infection.

The crotch portion of the thong also fits tightly against the external female genitalia. Thongs manufactured from a flexible fabrics that fold under the pressures of bodily wear and movement. On a daily cyclical basis, a female's pelvic floor can drop down (also known as prolapse) 7 millimeters (mm) as a result of gravity, and then retract during rest. This dropping increases the pressure between the external female genitalia and the fabric of the crotch portion. Under these pressures, the folded flexible fabrics cut into the sides of the wearer's labia or cut into the wearer's inner thigh nearby the labia. At times, the fabric of the undergarment folds into and bisecting the labia of the wearer, thereby applying localized pressure to the organs normally shielded by the labia, such as the urethra. Repeated, prolonged wear of a tightly-fitted crotch portion of the thong causes urethra crushing. Urethra crushing leads to partial closure of the urethra and incontinence.

Figure 2:
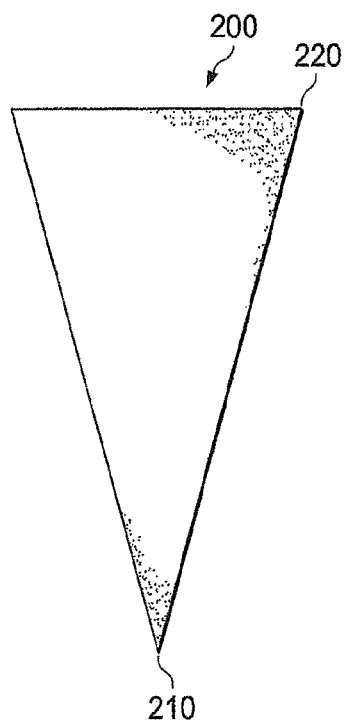

FIGS. 1 and 2 illustrate various designs of a pantyliner for absorbing menstrual fluid (i.e., sanitary napkin). FIG. 1 illustrates a pantyliner 100 that comprises the general shape of a long, thin strip rectangle overlayed one vertex of a triangle that has a shorter length than the rectangle. The triangle and rectangle include sharp vertices. The first end of the rectangle includes two vertices, both overlaying the triangle. The opposite, second end of rectangle includes two vertices 110a-110b, both disposed at the most posterior end of the pantyliner 100. The other two vertices 120a-120b of the triangle are disposed at the most anterior end of the pantyliner 100.

FIG. 2 illustrates a pantyliner 200 that comprises the general shape of an isosceles triangle 200 with an aspect ratio greater than one. The posterior end 210 of the pantyliner 200 includes one vertex, disposed a further distance away from the centroid (i.e., geometric center) of the triangle than the center of the anterior end 220 from the centroid. The wider, anterior end 220 comprises two vertices of the triangular shaped-pantyliner. The triangle includes sharp vertices.

During wear, the pantyliner 100, 200 is attached to the body-contacting side of the crotch portion of the thong. One problem with pantyliners, especially pantyliners 100, 200 for use with thong underwear, is their lack of ability to remain secured to such underwear and to stay in place. Thongs have little surface area of fabric at the rear portion and at the narrow posterior end of the crotch portion of the thong underwear for such pantyliners to attach. The narrow width of the posterior portion of the pantyliner 100, 200 has too little surface area to attach to the rear portion of the thong.

The posterior end 110a-b, 200 of the pantyliner 100, 200 is disposed in the wearer's perineum and anal areas. These areas of the body generate heat and sweat, because the areas are not exposed to much airflow during normal bodily movements, such as standing, sitting, walking, and running. As a result of the limited airflow across these areas of the body, heat does not dissipate as quickly as other more ventilated body areas. Sweat weakens the strength of the bond between the adhesive and the material of the crotch portion of the thong. In certain instances, sweat causes the pantyliner to detach from the material of the thong. Additionally, the area between the buttocks is sensitive and subject to a high degree of movement. In some instances, the detached posterior end 110a-110b, 210 of the pantyliner 100, 200 lightly reattaches to the buttocks of the wearer. In some instances, the detached posterior end 110a-110b, 210 of the pantyliner 100, 200 flaps back and forth between the buttocks during bodily movement, thereby providing an annoyance or irritant to this sensitive area of the wearer.

The pantyliner 100, 200 comprises a flat surface on the head-facing top side and on the foot-facing bottom. The flat surface makes the pantyliner 100, 200 apt to fold together with the material of wearer's undergarment. When the material of undergarment folds under the pressures of bodily movement and pelvic floor prolapse, the pantyliner 100, 200 does not resist the folding tendency of the material. Instead, the pantyliner 100, 200 folds with the material thereby adding pressure to the folded fabric that bisects the labia of the wearer.

Another problem with pantyliners 100, 200 is that the flat surface does not provide support to the pelvic floor of the wearer and does not resist pelvic floor prolapse.

Structural Support for Thong Undergarment

Figure 3:
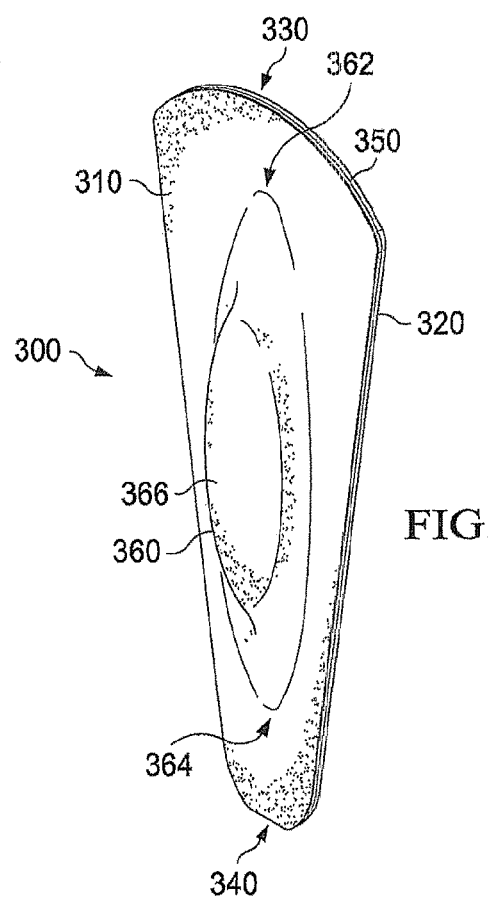
FIG. 3 illustrates an isometric view of a panty guard with a three-dimensional pelvic organ support for thong underwear in accordance with embodiments of the present disclosure.

FIG. 3 illustrates a panty guard 300 according to embodiments of the present disclosure. The panty guard 300 provides structural support for the crotch portion of a thong undergarment. The panty guard 300 provides a barrier between the wearer's skin and the fabric of the thong. That is, the panty guard 300 prevents the undergarment from touching the skin of the wearer's external genitalia or external pelvic organs. The material of the panty guard 300 includes one or any combination of natural, chemical, or synthetic fibers. The material of the panty guard 300 provides stiffness to the material of the undergarment and resistance against upward (e.g., headward, superior) pressure against the wearer's body. The panty guard 300 resists the tendency of the material of the undergarment to fold and bisect the labia of the wearer. The panty guard 300 can be worn throughout a day and overnight. The panty guard 300 is disposable. In certain embodiments, the panty guard is to be disposed after one use. Although certain details will be provided with reference to the components of the panty guard 300, it should be understood that other embodiments may include more, less, or different components.

Figures 4A, 4B:
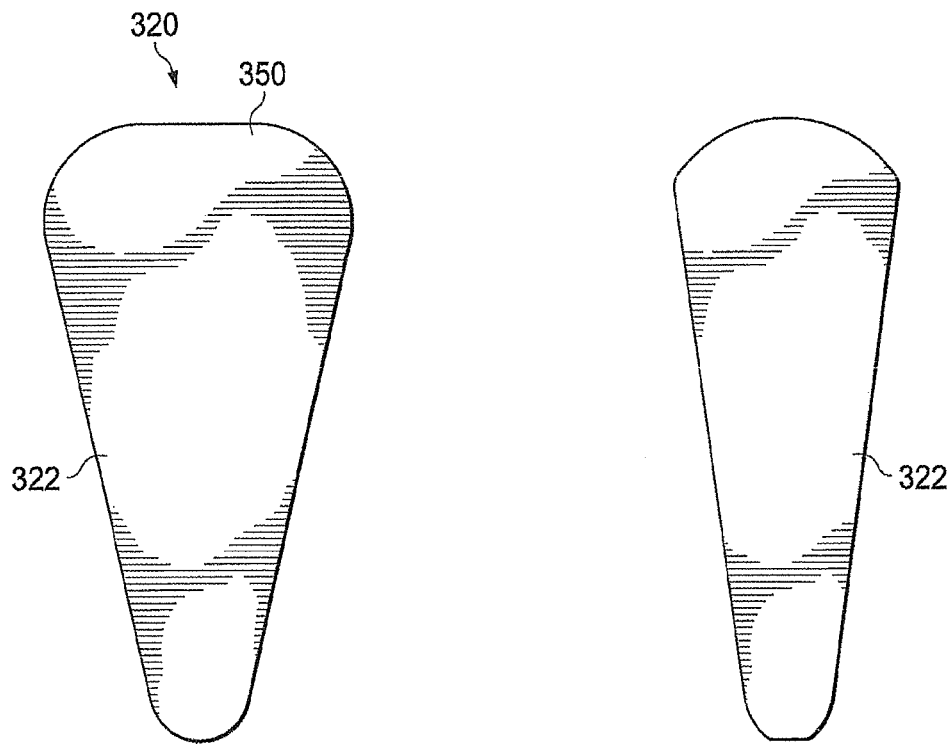
FIGS. 4A and 4B illustrate a bottom view of a panty guard with a three-dimensional pelvic organ support for thong underwear in accordance with embodiments of the present disclosure.

The panty guard 300 includes the general shape of multi-sided shape, such as an isosceles triangle with round vertices (as shown in FIG. 4A). In certain embodiments, the general shape of the panty guard 300 includes an isosceles trapezoid. That is, the panty guard 300 is substantially symmetrical along a (anterior-posterior) center axis. The panty guard 300 includes a posterior end 340 and an anterior end 330. In certain embodiments, the posterior end 340 includes one vertex of the triangle; and the anterior end 330 includes the remaining two vertices. In certain embodiments, the posterior end 340 includes the narrower base of the trapezoid between two vertices—the vertices are either rounded or chamfered. The anterior end 330 includes the wider base of the trapezoid between the remaining two vertices—the vertices are either sharp or rounded. The anterior end 330 of the trapezoid of the general shape of the panty guard 300 includes a circular segment immediately anterior to the wider base of the trapezoid. The chord length of the circular segment is substantially equal to the width of the wider base of the trapezoid. In certain embodiments, the width of the anterior end 330 is at least twice as wide as the width of the posterior end 340. For example, an anterior width of 2.2 inches and a posterior width of 0.4 inches. The aspect ratio of the panty guard 300 is greater than one. That is, the (anterior-posterior) length of the panty guard 300 is greater than the (left-right) width. For example, a width of 2.2 inches and a length of 5.9 inches. The left and right sides of the panty guard 300 are shown as straight sides. In certain embodiments, the left and right sides of the panty guard 300 are concave to trace the round, curved contours of the wearer's inner thighs.

The panty guard 300 includes a top surface 310 and a bottom surface 320, both with a same-shaped, same-sized perimeter. The panty guard includes one or more layers of material. For example, the top surface 310 is the top layer 310. The top surface 310 comprises a material that is non-abrasive to skin, such as cotton, or other material from which the body-contacting surface of pantyliners are constructed. In certain embodiments, the top surface 310 comprises a fluid permeable material that absorbs liquid and allows air to flow through, such as a cotton weave. A female secretes approximately one teaspoon (4.929 milliliters) of vaginal moisture each day. In certain embodiments, the material of the top surface 310 is capable of absorbing at least one teaspoon of liquid. In certain embodiments, the top surface 310 material includes a moisture wicking material that attracts moisture away from the surface of the wearer's skin and moves to moisture down to a lower layer, such as to the bottom layer 350.

In certain embodiments, the panty guard 300 includes a middle layer (not shown) between the top surface 310 and the bottom layer 350. The middle layer comprises a moisture-wicking material that wicks the moisture from top surface 310 down into the middle layer. In certain embodiments, middle layer protects the female genital organs from bacteria. For example, the middle layer includes a material that removes bacteria from the top surface 310 and draws the bacteria into the middle layer. As another example, the middle layer material includes an anti-bacterial substance that retards growth or kills bacteria.

Anatomically Correct 3D Female Pelvic Organ Support

In certain embodiments, the panty guard 300 includes a pelvic organ support (POS) 360. The shape of the POS 360 is anatomically correct to provide three dimensional (3D) support to the pelvic organs of a woman. The POS 360 counteracts the downward gravitational pull on the pelvic organs. The PUS 360 counteracts, in 3D, the forces of loose pelvic floor muscles. In certain embodiments, the POS 360 holds up the pelvic floor, helping the pelvic floor bear the load of gravity or forces. The shape of POS 360 matches the shape of a female's external genital organs from the morning's initial shape and position to the evening's shape and position due to a nominal drop (up to 7 mm). The perimeter of the POS 360 mimics the shape of the perimeter of a female's pelvic floor. The topography of the POS 360 complements the vertical dimension contours of a female's external genital organs. The PUS 360 prevents the material of wearer's undergarment, alone or together with a panty guard 300 or pantyliner 100, 200, from folding into or otherwise bisecting the labia of the wearer. In the same manner, the PUS 360 prevents a crushing of the wearer's urethra by the material of wearer's undergarment alone or together with a panty guard 300 or together with a pantyliner 100, 200.

In certain embodiments, the perimeter of the PUS 360 includes a multi-sided shape. For example, the shape of two isosceles triangles that share a base (together, a kite shape)—the width of the POS 360 is the width of the triangles' shared base. The isosceles triangles within the kite include rounded vertices. The posterior-pointing triangle includes an aspect ratio greater than one. In certain embodiments, the perimeter of the PUS 360 includes a rounded shape, such as an ellipse, oval, or lens. In certain embodiments, the width of the POS 360 is proportionally smaller than the width of the panty guard 100. In other embodiments, the aspect ratio of the POS 360 is greater than the aspect ratio of the panty guard 300. That is, the length of the POS 360 compared to the narrow width of the POS 350 is disproportionately longer than the length of the panty guard 300 compared to the width of the panty guard 300. The shape of a female pelvic floor does not vary much from woman to woman, regardless of the height or weight of the woman. Various embodiments of the POS 360 include different lengths of the POS 360 to provide greater or less coverage of the female pelvic organs to meet user preferences. For example, in certain embodiments, the length of the POS 360 spans the entire length of a woman's external genital organs. In certain embodiments, the length of the POS 360 spans the entire length of a woman's external genital organs and expends anteriorly (tapering forward) to provide added coverage. In one embodiment, the POS 360 perimeter dimensions include a length of approximately 4.1 inches and a width of approximately 1.15 inches.

The POS 360 is disposed at the center of the panty guard 300. That is, the axis of symmetry (i.e., the posterior-anterior center axis) of the POS 360 is collinear with the axis of symmetry of panty guard 300. The POS 360 includes an anterior end 362 and a posterior end 364. For example, in a multi-sided shaped POS 360, the posterior end 364 includes one rounded vertex of the triangle. The anterior end 362 includes the remaining two vertices. In certain embodiments, the perimeter of the posterior end 364 vertices is within, and does not abut the perimeter of the top surface 310 of the panty guard 310. In other embodiments, the perimeter of the posterior end 364 vertices meets the perimeter of the top surface 310 of the panty guard 310. In certain embodiments, the center (i.e., centroid; geometric center) of the POS 360 is posterior to the geometric center of the panty guard 300.

Although certain details will be provided with reference to the components of the POS 360, it should be understood that other embodiments may include more, less, or different components. In certain embodiments, the POS 360 is disposed on top of the top surface 310. In certain embodiments, the POS 360 is independent from the panty guard 300. As an independent device, a wearer may adhere the bottom surface of the PUS 360 to the top surface 310 of the panty guard 300, or to the body-contacting side of the crotch portion of the undergarment. For example, in an independent embodiment, the bottom surface POS 360 includes an adhesive such as the adhesive on the bottom surface 320 of the panty guard 300. In certain embodiments, the bottom surface of the POS 360 is the same-sized, same-shaped perimeter as the top surface of the POS 360. In certain embodiments, the perimeter of the bottom surface is larger than the perimeter of the top surface of the POS 360. In embodiments, wherein the POS 360 is disposed on above the top surface 310 of the panty guard, or as an independent device, the top surface of the POS 360 comprises a material that is non-abrasive in physical contact with the skin of the female genitalia. An example of a non-abrasive material includes cotton, or other material from which the body-contacting surface of pantyliners are composed.

Figure 5:
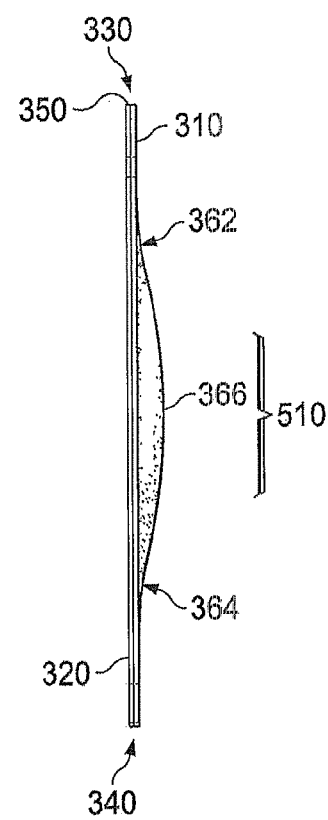
FIG. 5 illustrates a side view of a three-dimensional structural support for thong underwear in accordance with embodiments of the present disclosure.

The POS 360 includes a filling material, a frame, or both. In certain embodiments, the frame surrounds the filling material. In certain embodiments, the frame includes one or more orifices to be into which the filling material is packed. The frame forms and maintains the shape of the POS 360. The frame provides a raised surface for the top of the POS 360, as shown in FIG. 5. In certain embodiments, the frame provides a flat bottom for the PUS 360. In certain embodiments, the frame comprises the top 310 and bottom 350 layers of the panty guard 300. In certain embodiments, the frame comprises plastic, polymer, or other impenetrable semi-rigid material. In certain embodiments, the top of the frame includes one or more pores that provide a via for fluid to fall onto an absorptive material disposed below the top of the frame.

The filling material of the POS 360 includes malleable material that rides comfortably against the wearer's genitalia. Examples of filling material include cotton, foam, gel, and gel with cooling properties, or other flexible natural or synthetic fibers. The filling material of the POS 360 is moldable into the shape of external genital organs of the female body. For example, when a hollow frame forms and maintains the shape of the POS, the filling material is flexible to substantially occupy the hollow space within the frame. In certain embodiments, the POS 360 includes one or more moisture absorbing materials. As an example, a moisture absorbing frame is packed with a filling material composed of impervious silicone beads. In this example, the filling material establishes an interior and an inferior layer disposed beneath the absorptive frame. In certain embodiments, the frame and the filling material include an absorptive material.

In certain moisture absorbing embodiments of the POS 360, moisture causes the material of the POS 360 to expand sideways (left-right or posterior-anterior) only. That is, in certain embodiments, the POS 360 is configured to maintain a predetermined thickness and does not expand vertically. For example, certain embodiments maintain a 7 mm thickness to support the expected daily prolapse. In certain embodiments, the POS 360 does not expand beyond a predetermined thickness. In certain embodiments, the POS 360 is capable of absorbing at least 1 teaspoon of fluid.

In certain embodiments, the POS 360 includes multiple layers of material. For example, the POS 360 includes a first, top layer of cotton and a second layer of gel. Examples of materials for the layers of the POS 360 can include one or a combination of a moisture wicking material, a breathable material, an absorptive material, fluid resistant material, a fluid impermeable material, or other suitable material. In certain embodiments, the material of the POS 360 draws bacteria into a lower layer of the POS 360, such as a middle or bottom layer 350. In certain embodiments, the material of the POS 360 provides flora to the vaginal area of the wearer to restore or maintain health of the wearer's organs. In certain embodiments, the material of the POS 360 provides medicine to the vaginal area of the wearer, such as a drug applied topically or aromatically.

As a specific example, the POS 360 includes a first, top layer of material with a unidirectional fluid permeability characteristic and a second, lower layer of material with moisture wicking characteristics. In this example, the unidirectional permeable material absorbs vaginal fluids from the skin of the wearer, and the moisture wicking second layer attracts the absorbed fluids down, through the first layer into the second layer. The top layer is substantially impervious (semi-impervious or completely impervious) to fluids beneath the top layer, such as fluids within the second layer. If a lower layer of the POS 360 includes fluids channeled from the wearer's anal area, the top layer will not conduct fluids up to the skin of the wearer. The top layer of the POS 360 breaks the fluid channel from the wearer's anal area to the wearer's vaginal area. The top layer of the POS 360 averts conditions that produce infection and prevents the spread of bacteria.

In certain embodiments, the top surface 310 of the panty guard 300 is flat. In other embodiments, the top surface 310 includes a raised center. For example, when the panty guard 300 includes a POS 360, the top surface 310 provides a frame to hold the shape of the top of the POS 360 and blankets the top of the POS 360. That is, the raised center of the top surface 310 complements the perimeter of the external pelvic organs of a woman. The raised center of the top surface 310 matches the topographical contours of the POS 360 inserted or disposed beneath the top surface 310. In such an embodiment, the PUS 360 is the middle layer between the top layer 310 and the bottom layer 350.

FIGS. 4A and 4B illustrate the bottom surface 320 of a panty guard 300 according to embodiments of the present disclosure. The shape of the perimeter of the bottom surface 320a in FIG. 4A includes an isosceles triangle. The shape of the perimeter of the bottom surface 320b in FIG. 4B includes an isosceles trapezoid topped with a circular segment. The bottom surface 320 is the bottom of the bottom layer 350. In certain embodiments, the bottom surface 320 includes a material that comprises one or a combination of the following characteristics: breathable, fluid resistant, and impervious to fluid. The bottom surface 320 includes a positioning adhesive protected by a cover 322. The positioning adhesive attaches the panty guard 300 to undergarment and holds the panty guard 300 in place. In certain embodiments, the adhesive comprises a glue, such as a chemically neutral adhesive. In certain embodiments, as shown in FIG. 4B, the adhesive covers the entire bottom surface 320b of the panty guard 300. In certain embodiments, as shown in FIG. 4A, the adhesive covers a majority of the bottom surface 320a of the panty guard 300. The cover 322 protects the positioning adhesive from attaching to an object prior to use. Prior to use, all areas of the adhesive is covered by the cover 322. Compared with the sharp vertices of pantyliners 100, 200, the round vertices of the panty guard 300 requires more force to lift the adhesive to detach the panty guard from the material of the undergarment. Compared with the sharp vertices of pantyliners 100, 200, the round vertices increase the surface area of the panty guard that adheres to the material of the undergarment. For example, at the rounded vertex of the posterior end 340, the bottom surface 320 is completely covered by adhesive, thereby increasing the surface area of adhesive attached to the narrow posterior end of the crotch portion of the thong. In addition to the increased surface area, the full adhesive coverage of the rounded vertex of the posterior end 340 further resists lift and detachment, thereby protecting this sensitive area of the wearer from an annoying, irritating sensation of a flapping sticker.

FIG. 5 illustrates a side view of a POS 360 disposed atop the panty guard 300 for thong underwear in accordance with embodiments of the present disclosure. The posterior end is located at the bottom of the drawing, and the anterior end is located at the top of the drawing. In certain embodiments, the bottom surface of the POS 360 complements the shape of the layer of the POS 360 disposed immediately beneath the POS 360. For example, the bottom surface of the POS 360 may be flat to the bottom layer 350 of the panty guard 300.

The top surface 366 of the POS 360 includes a raised surface. The topography of the top surface 366 is anatomically correct to complement or pair with the rise and fall contours of female genitalia. The thickest portion 510 of the POS 360 is closer the posterior end 364 of the POS 360 than to the anterior end 362. The thickest portion 510 of the POS 360 includes a central peak, disposed on the top surface 366 and located at the centroid of the thickest portion 510. As such, the central peak is also disposed at the center of the perimeter of the POS 360. In certain embodiments, the thickest portion 510 resembles a plateau. A top view of the plateau includes a round shape with at least a longitudinal axis of symmetry, such as an ellipse, oval, or lens. For example, certain oval shaped plateau tops are not symmetrical about the axis orthogonal to the longitudinal axis of symmetry, and are more pointed toward the anterior end 362. A top view of the topography of the top surface includes concentric contour lines of the same round shape as the thickest portion 510, down to the plane of the perimeter. In certain embodiments, the concentric contour line on the same plane as the perimeter of the POS 360 span a length of substantially 2.2 inches and a width of substantially 1.15 inches. The top surface 366 of the POS 360 includes at least two slopes. In certain embodiments, the rise from the anterior end 362 to the thicket portion 510 to the thickest portion is substantially the same steepness as the slope from the posterior end 364 to the thickest portion 510. In other embodiments, the rise from the anterior end 362 to the thickest portion 510 is less steep than the slope from the posterior end 364 to the thickest portion 510. The height of the thickest portion is less than one inch. In certain embodiments, the height of the thickest portion is less than three-fourths of an inch (0.75 inches). In one embodiment, the height of the thickest portion is substantially one-half inch (0.5 inches).

Figure 6:
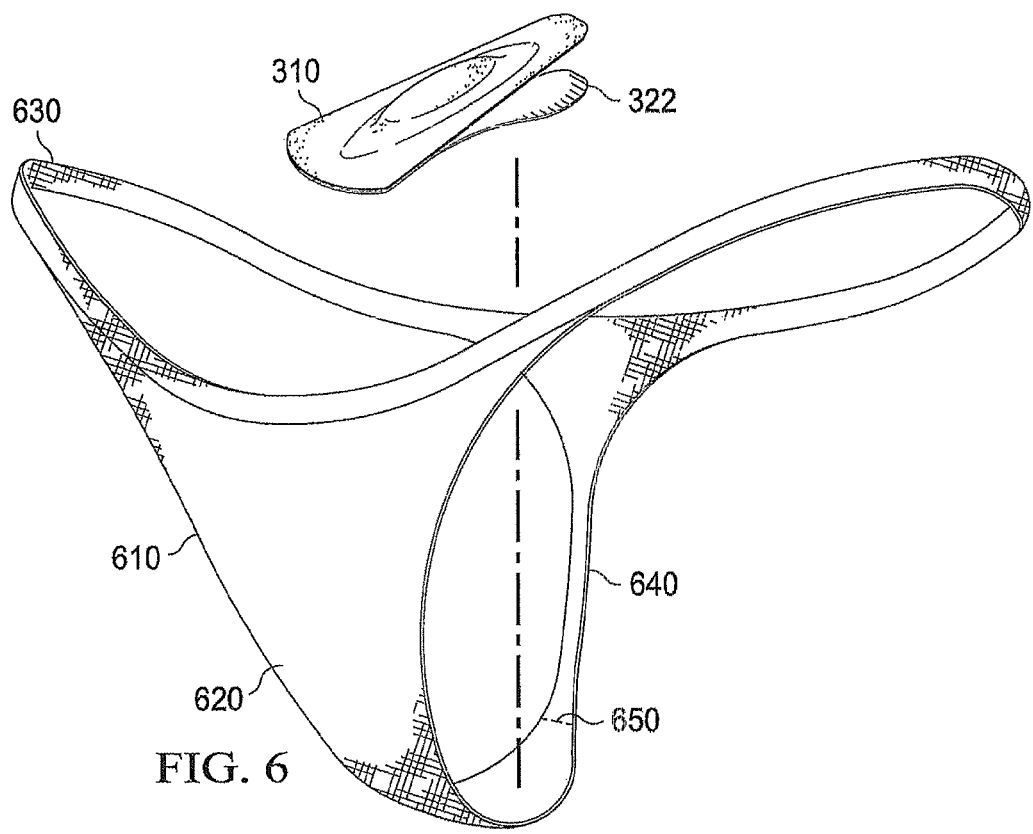
FIG. 6 illustrates an exploded view of a panty guard with a three-dimensional pelvic organ support to be inserted into a crotch portion of a thong underwear garment in accordance with embodiments of the present disclosure.
Figure 7:
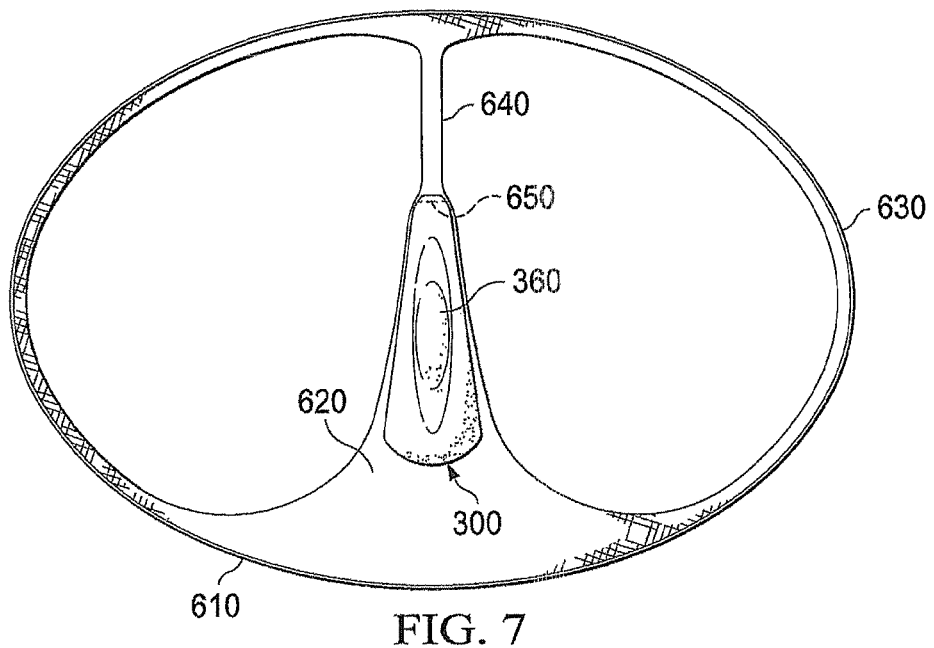
FIG. 7 illustrates a three-dimensional structural support adhered to the crotch portion of a thong underwear garment in accordance with embodiments of the present disclosure.

FIGS. 6 and 7 illustrate various views of panty guard 300 with a POS 360 for placement within thong underwear in accordance with embodiments of the present disclosure. FIG. 6 illustrates an exploded perspective view of the thong underwear 610 and the panty guard 300 with a POS 360. The thong under wear includes a crotch portion 620, a waistband 630, and a rear portion. To wear the panty guard 300, a user removes the cover 322, thereby exposing the adhesive of the bottom surface 320. Next, the user presses the panty guard 300 onto the body-contacting side of the crotch portion 620 of the thong underwear 610. The panty guard 300 is placed within the thong underwear 610 without covering the anus. In the case of a long length panty guard 300, the user places the panty guard 300 within the thong underwear 610 to cover the anus.

FIG. 7 illustrates a top view of the panty guard 300 with a POS 360 adhered to the crotch portion of the thong underwear 610 in accordance with embodiments of the present disclosure. In the design of thong underwear 610 shown, the seam 650 that joins the crotch portion 620 to the rear portion 640 is hidden because the placement of the seam 650, disposed at a string width of the crotch portion 620, is more anterior than the posterior end 340 of the panty guard 300. That is, the user, places the panty guard 300 over the seam 650 to reduce irritation. In other designs of thong underwear, where the seam 650 is disposed at a wider portion of the underwear, the user places the panty guard 300 anterior to the seam 650, and the seam is visible.

Although various features have been shown in the figures and described above, various changes may be made to the figures. For example, the size, shape, arrangement, and layout of components shown in FIGS. 3 through 7 are for illustration only. Each component could have any suitable size, shape, and dimensions, and multiple components could have any suitable arrangement and layout. Also, various components in FIGS. 1 through 7 could be combined, further subdivided, or omitted and additional components could be added according to particular needs. Further, each component in a device or system could be implemented using any suitable structure(s) for performing the described function(s). Although an exemplary embodiment of the present disclosure has been described in detail, those skilled in the art will understand that various changes, substitutions, variations, and improvements disclosed herein may be made without departing from the spirit and scope of the disclosure in its broadest form.

None of the description in the present application should be read as implying that any particular element, step, or function is an essential element which must be included in the claim scope: the scope of patented subject matter is defined only by the allowed claims. Moreover, none of these claims are intended to invoke paragraph six of 35 USC §112 unless the exact words "means for" are followed by a participle.

What is claimed is:

1. A panty guard comprising:
    a bottom portion configured for adherence to a crotch of thong underwear;
    a pelvic organ support (POS) positioned atop the bottom portion, the POS comprising a topography complementing external female genital organs, the topography comprising cross-sectional perimeters of concentric vertical ascensions extending from the bottom portion to a top of the POS at the thickest portion of the POS, the concentric vertical ascensions having the same shape, and the POS containing absorptive material configured to absorb fluid from the top towards the bottom portion; and
    wherein the panty guard contains an external perimeter with an anterior end and a posterior end, the anterior end having a width that is larger than a width of the posterior end; and
    wherein the edges between anterior end and the posterior ends are straight.

2. The panty guard of claim 1, wherein the width of the anterior end is at least twice as wide as the width of the posterior end.

3. The panty guard of claim 1, wherein the shape of the cross-sectional perimeters of the concentric vertical ascensions are at least one of an oval ellipse or a lens.

4. The panty guard of claim 1, wherein a portion of the panty guard includes medicine for the external female genital organs.

5. The panty guard of claim 1, wherein a portion of the panty guard includes an anti-bacterial configured to prevent a spread of bacteria through the panty guard.

6. The panty guard of claim 1, wherein the panty guard is configured to provide an upward pressure to the external female genital organs.

7. The panty guard of claim 1, wherein the POS includes at least two layers where a frame is disposed between such layers.

8. A panty guard comprising:
    a bottom portion configured for adherence to a crotch of thong underwear; and
    a pelvic organ support (POS) positioned atop the bottom portion, the POS comprising a topography complementing external female genital organs, the topography comprising cross-sectional perimeters of concentric vertical ascensions extending from the bottom portion to a top of the POS at the thickest portion of the POS, the concentric vertical ascensions having the same shape, and the POS contains absorptive material configured to absorb fluid from the top towards the bottom portion.

9. The panty guard of claim 8, wherein
    the panty guard is configured to absorb, using at least the absorptive material of the POS, less than approximately one teaspoon of fluid.

10. The panty guard of claim 9, wherein the shape of the cross-sectional perimeters of the concentric vertical ascensions are at least one of an oval ellipse or a lens.

11. The panty guard of claim 8, wherein the topography is configured to resist daily prolapse of the external female genital organs.

12. The panty guard of claim 8, wherein a top surface of the POS is configured for placement in physical contact with the external female genital organs.

13. The panty guard of claim 8, wherein a portion of the panty guard includes medicine for the external female genital organs.

14. The panty guard of claim 8, wherein a portion of the panty guard includes an anti-bacterial configured to prevent a spread of bacteria through the panty guard.

15. The panty guard of claim 8, wherein the panty guard is configured to resist a bisection of the external female genital organs.

16. The panty guard of claim 8, wherein the panty guard is configured to provide an upward pressure to the external female genital organs.

17. A panty guard comprising:
    a bottom portion configured for adherence to a crotch of thong underwear; and
    a pelvic organ support (POS) positioned atop the bottom portion, the POS comprising a topography with cross-sectional perimeters of concentric vertical ascensions extending from the bottom portion to a top of the POS at the thickest portion of the POS, the concentric vertical ascensions having the same shape; wherein the POS contains absorptive material configured to absorb fluid from the top towards the bottom portion.

18. The panty guard of claim 17, wherein the shape of the cross-sectional perimeters of the concentric vertical ascensions are at least one of an oval ellipse or a lens.

* * * * *